US008883221B2

(12) United States Patent
Bellmann et al.

(10) Patent No.: US 8,883,221 B2
(45) Date of Patent: Nov. 11, 2014

(54) MICRONUTRIENT COMBINATION PRODUCT FOR USE AS A DIETETIC FOOD SUPPLEMENT IN AGE-RELATED MACULAR DEGENERATION

(75) Inventors: Guenter Bellmann, Berlin (DE); Gudrun Claus-Herz, Berlin (DE)

(73) Assignee: Bausch & Lomb Incorporated, Rochester, NY (US)

( * ) Notice: Subject to any disclaimer, the term of this patent is extended or adjusted under 35 U.S.C. 154(b) by 1821 days.

(21) Appl. No.: 10/583,953

(22) PCT Filed: Dec. 17, 2004

(86) PCT No.: PCT/EP2004/053579
§ 371 (c)(1),
(2), (4) Date: May 10, 2007

(87) PCT Pub. No.: WO2005/063051
PCT Pub. Date: Jul. 14, 2005

(65) Prior Publication Data
US 2008/0014287 A1    Jan. 17, 2008

(30) Foreign Application Priority Data
Dec. 23, 2003  (DE) .............................. 203 20 101 U

(51) Int. Cl.
| A61K 33/34 | (2006.01) |
| A61K 33/30 | (2006.01) |
| A61K 31/355 | (2006.01) |
| A61K 31/375 | (2006.01) |
| A61K 31/047 | (2006.01) |
| A61K 47/00 | (2006.01) |
| A23L 1/304 | (2006.01) |
| A23L 1/30 | (2006.01) |

(52) U.S. Cl.
CPC ............... *A23L 1/304* (2013.01); *A23L 1/3002* (2013.01); *A23V 2002/00* (2013.01)
USPC ........... 424/638; 424/630; 424/641; 424/643; 514/458; 514/474; 514/729; 514/738; 514/739; 514/769; 514/770; 514/772; 514/772.3; 514/772.4; 514/772.5; 514/774; 514/777; 514/778; 514/781; 514/782; 514/783; 514/784; 514/785; 514/786

(58) Field of Classification Search
None
See application file for complete search history.

(56) References Cited

U.S. PATENT DOCUMENTS

| 5,948,443 A * | 9/1999 | Riley et al. ..................... 424/643 |
| 6,579,544 B1 * | 6/2003 | Rosenberg et al. ........... 424/736 |
| 6,582,721 B1 | 6/2003 | Lang | |
| 2002/0172721 A1 * | 11/2002 | Boulos et al. ................. 424/646 |
| 2002/0182266 A1 | 12/2002 | Bartels et al. | |

FOREIGN PATENT DOCUMENTS

| EP | 1214893 A1 | 6/2002 |
| GB | 2301775 A | 12/1996 |
| WO | WO 03/063848 A1 | 8/2003 |
| WO | WO 03/103646 A1 | 12/2003 |

OTHER PUBLICATIONS

Dr. Billy R. Hammond et al., "Density of the Human Crystalline Lens is Related to the Macular Pigment Carotenoids, Lutein and Zeaxanthin," Optometry and Vision Science, American Academy of Optometry, vol. 74 (No. 7), p. 499-504, (Jul. 1997).

* cited by examiner

*Primary Examiner* — Abigail Fisher
*Assistant Examiner* — Frank Choi
(74) *Attorney, Agent, or Firm* — Toan P. Vo

(57) ABSTRACT

Micronutrient combination product, wherein the micronutrient combination product comprises zeaxanthin, lutein, zinc and copper.

8 Claims, No Drawings

MICRONUTRIENT COMBINATION PRODUCT FOR USE AS A DIETETIC FOOD SUPPLEMENT IN AGE-RELATED MACULAR DEGENERATION

The present invention relates to a micronutrient combination product. Said micronutrient combination product can, for example, be employed for a supplementary balanced diet in cases of age-related macular degeneration.

It is commonly known that the visual process exerts great strain on the eye. The impact of light and oxygen leads to the formation of so-called "free radicals", which can lead to pathological alterations in the retina.

Furthermore, it is commonly known that many external influences, like imbalanced diet, smoking and drinking alcohol, environmental pollution, stress or UV radiation, can lead to a release of radicals. However, the normal processes of metabolism also cause a short-term release of highly active substances, which can strain and harm the body. For degrading said "free radicals", the body has its own "anti-oxidative" protection system, wherein the vitamins C and E, the vitamin-like carotenoids lutein and zeaxanthin, and the trace element zinc play essential parts. The system offers optimal protection only if all its active components are available in sufficient quantities.

The visual process and the permanent impact of light exert an increased measure of oxidative strain on the eye. Thus, the eye has an increased demand for adequate supply with the anti-oxidative substances vitamin C, vitamin E, zinc and the vitamin-like carotenoids lutein and zeaxanthin.

The macula of the eye is among those organs that require particularly high concentrations of the carotenoids lutein and zeaxanthin. The medical term "Macula lutea" denotes the center of the retina, i.e. the point of sharpest vision. It is here that the most sensitive visual cells of the eye are located.

In cases of a long-term lack of micronutrients in the macula, the risk of developing "age-related macular degeneration" (AMD) increases. AMD results in a diminution of the strength of vision, in the worst case leading to blindness.

The vitamin preparations known in the art contain various, frequently high-dosed, compositions of vitamins and trace elements, which, however, are not directed to supply the macula of the eye. Thus, a large part of said compositions contain large proportions of anti-oxidatively acting vitamins and trace elements, but not lutein and zeaxanthin. One disadvantage of said preparations is their lack of supplying the macula, which has a central function in the visual process.

It is a further disadvantage of customary anti-oxidative preparations that the age-dependency of the need for vitamins and minerals is not adequately considered. Particularly at an advanced age, deficiency symptoms caused by inadequate supply owing to undernourishment and malnutrition or disease can rapidly become noticeable, in particular in view of diseases like AMD, which are insufficiently accounted for by preparations adjusted thereto.

There is thus a need for a means counteracting a deficient supply of the macula by means of micronutrients. Furthermore, there is a need for a means, which per se does not evoke deleterious side effects and can both harmlessly serve for preventing deficiency symptoms and can furthermore be employed in cases of already prevailing age-related macular degeneration.

It is thus a problem underlying the present invention to provide a means for overcoming the previously mentioned disadvantages in the art. In particular, it is a problem underlying the present invention to provide a means offering comprehensive supply of the macula.

This problem is solved by means of a micronutrient combination product, wherein the micronutrient combination product comprises zeaxanthin, lutein, zinc and copper.

It has surprisingly been shown that the macula was significantly strengthened by optimized combination of the vitamin-like carotenoids lutein and zeaxanthin. It has furthermore surprisingly been shown that the vitamin-like carotenoids used, which had been optimized according to the present invention, effected an improved preventive protection of the macula due to their capability of intercepting radicals present.

Without intending to be bound by any particular theory, it is assumed that the vitamin-like carotenoids lutein and zeaxanthin selectively accumulate at high concentrations in the macula and thus protect this region by means of filtering light and intercepting harmful "free radicals". The aimed delivery of these essential micronutrients can thus contribute to protecting the eye from the development of age-related macular degeneration or to decelerate its progression.

A further great advantage of the micronutrient combination product according to the present invention is put into effect by lutein being capable of increasing the density of macular pigments.

Furthermore, the micronutrient combination product according to the present invention contains copper, which counteracts a potential copper deficiency that can result from the intake of zinc. It is an advantage that the micronutrient combination product according to the present invention comprises an extremely low-dosed copper proportion due to the zinc proportion which, according to the present invention, is also low as well as to the resulting significant decrease of the side effects caused by zinc.

Combining the vitamin-like carotenoids lutein and zeaxanthin with the trace elements zinc and copper advantageously provides a micronutrient combination product providing comprehensive and balanced supply of the macula. Furthermore, the co-ordinated administration of the carotenoids and trace elements safely prevents overdosing and provides for a co-ordinated supply.

The micronutrient combination product according to the present invention can be employed for a supplementary balanced diet or for accompanying administration, for example in the treatment of age-related macular degeneration.

In preferred embodiments, the micronutrient combination product contains the following agents, as related to the total weight of the micronutrient combination product:
  a. 0.5 weight % to 5 weight %, preferably 0.75 weight % to 2.5 weight %, particularly preferably 0.8 weight % to 1.2 weight %, lutein;
  b. 0.01 weight % to 0.1 weight %, preferably 0.02 weight % to 0.08 weight %, particularly preferably 0.04 weight % to 0.06 weight %, zeaxanthin;
  c. 0.005 weight % to 0.1 weight %, preferably 0.01 weight % to 0.08 weight %, particularly preferably 0.015 weight % to 0.05 weight %, copper;
  d. 0.5 weight % to 5 weight %, preferably 1 weight % to 2.5 weight %, particularly preferably 1.3 weight % to 2 weight %, zinc.

In the sense of the present invention, the term "agent" is understood to denote micronutrients. Micronutrients are substances contained in the micronutrient combination product, preferably selected from the group comprising zeaxanthin, lutein, zinc, copper, vitamin E and/or vitamin C.

Advantageously, the micronutrient combination product contains at least one vitamin, preferably vitamin C and/or vitamin E. In preferred embodiments, the micronutrient combination product contains, as related to the total weight of the micronutrient combination product: 5 weight % to 30 weight %, preferably 10 weight % to 20 weight %, particularly preferably 10 weight % to 15 weight % vitamin C and/or 0.5 weight % to 3 weight %, preferably 1 weight % to 2 weight %, particularly preferably 1.0 weight % to 1.5 weight % vitamin E. In a particularly preferred embodiment, the micronutrient combination product contains lutein, zeaxanthin, zinc, copper, vitamin C, and vitamin E.

In a further preferred embodiment, the micronutrient combination product comprises the following agents, as related to the total weight of the micronutrient combination product:
   a. 1 weight % lutein;
   b. 0.05 weight % zeaxanthin
   c. 12.5 weight % vitamin C;
   d. 1.25 weight % vitamin E;
   e. 0.033 weight % copper;
   f. 1.67 weight % zinc.

Advantageously, the micronutrient combination product contains copper and zinc in form of salts. Suitable salts are, for example, selected from the group comprising sulfates and/or oxides. In particularly preferred embodiments, zinc and copper are available in form of zinc gluconate and copper (II) gluconate. By means of employing zinc gluconate and copper (II) gluconate, bioavailability is improved in an advantageous manner.

For instance, zinc gluconate exhibits a better resorption than the frequently used zinc oxide. Furthermore, zinc gluconate can also exhibit a better resorption than zinc sulfate. Said increased bioavailability facilitates the use of a far smaller quantity of zinc as daily dose or single dose, thereby significantly decreasing the danger of side effects. Zinc gluconate, in particular, exhibits a distinctly better resorption than the also frequently used zinc oxide. It is assumed that the supply of the macula with zinc is improved by means of employing zinc gluconate. It is further conceivable, that the required zinc proportion of the micronutrient combination product can be reduced by means of employing the readily resorbable zinc gluconate, thereby avoiding potential overdosing.

Advantageously, the micronutrient combination product, which is formulated in an optimized manner with respect to its components, comprises the following agents, as related to one daily dose of the micronutrient combination product:
   a. 2 mg to 40 mg, preferably 6 mg to 24 mg, lutein;
   b. 0.1 mg to 2 mg, preferably 0.3 mg to 1.2 mg, zeaxanthin;
   c. 50 mg to 500 mg, preferably 75 mg to 300 mg, vitamin C;
   d. 2 mg to 60 mg, preferably 7.5 mg to 30 mg, vitamin E;
   e. 0.02 mg to 2 mg, preferably 0.2 mg to 0.8 mg, copper;
   f. 1 mg to 80 mg, preferably 10 mg to 40 mg, zinc.

In its function as a means for a supplementary balanced diet, the micronutrient combination product according to the present invention contains zeaxanthin, which, in a balanced combination with lutein, the trace elements zinc and copper, and further anti-oxidatively acting vitamins, contributes to preventing damage done by radicals as well as to the effect of the means according to the present invention by means of a balanced supply of the macula, thereby positively influencing an improvement of vision at an advanced age and impeding the development of age-related macular degeneration. It has surprisingly been shown that, in particular, employing zeaxanthin in accordance with the present invention in combination with zinc positively influences the supply of consumers as opposed to the use of monopreparations. Due to employing the vitamin-like carotenoids having anti-oxidant properties in accordance with the present invention in combination with zinc and copper, the micronutrient combination product has an improved nutritive or dietetic effect.

The advantageous properties result from the optimized selection of individual components, which have been selected specifically for counteracting oxidative damage of the macula done by radicals and equalize a deficit of antioxidants caused by nutritional deficits or risk factors like smoking and drinking alcohol, environmental pollution, stress or UV radiation.

A further advantage of the micronutrient combination product according to the present invention is the synergistic effect with respect to a comprehensive integral supply of the macula. The macula is strengthened by means of the optimized combination of the vitamins and trace elements, in particular of the vitamin-like carotenoids lutein and zeaxanthin as well as zinc and copper.

It is a further advantage that the dosages of the means according to the present invention do not cause harmful side effects and can serve for prophylaxis as well as for equalizing a prevailing supply deficit of the macula. This is advantageous for a supplementary balanced diet as well as for dietetic treatment of age-related macular degeneration. A positive effect shows, in particular, by means of a supplementary balanced diet or dietetic administration in cases of deficiency conditions and by means of preventing the development of a deficiency situation, which can lead to age-related macular degeneration.

Embodiments of the micronutrient combination product that do not contain further carotenoids can be suitable. Administration of further carotenoids can have a disadvantageous effect on resorption and/or cause a potential interaction of the carotenoids.

For instance, an embodiment of the micronutrient combination product, which is free of beta-carotene and/or copper oxide, can be suitable according to the present invention. Oral intake of beta-carotene at high dosages can, in particular in smokers, lead to damage in connection with drugs. The micronutrient combination product according to the present invention can be free of beta-carotene. In an advantageous manner, an embodiment of the micronutrient combination product that is free of beta-carotene can create the possibility of also being taken by smokers.

The micronutrient combination product can be available in form of a solid, a liquid and/or a gel; preferably the micronutrient combination product is available in forms of preparation selected from the group comprising tablets, film-coated tablets, sugar-coated pills, capsules, powders, granulates, solutions and/or effervescent tablets having the same or a different composition.

In preferred embodiments, the micronutrient combination product is available in a solid dosage form, wherein the core of the dosage form constitutes 200 mg to 1000 mg, preferably 400 mg to 800 mg, and preferably 600 mg. The core of the dosage form can preferably be coated with a film.

Manufacturing the dosage forms can be conducted according to general standard methods.

The micronutrient combination product according to the present invention is preferably available in form of a tablet, in particular a film-coated tablet. Preferably, the tablet comprises a tablet core, which can be coated with a film.

The micronutrient combination product, in particular the tablet core, can contain further adjuvants, preferably selected from the group comprising lactose, povidone, cellulose and/or cellulose derivatives, microcrystalline cellulose, starch and/or starch derivatives, magnesium stearate, stearic acid, gelatin, sodium aluminum silicate, silica, maltodextrin, dextrose, talcum, titanium dioxide, calcium carbonate, vegetable fats, tricalcium phosphate, antioxidants, stabilizers, Arabic gum, calcium phosphates, calcium silicate, sucrose, sodium citrate, citric acid and/or gustatory corrigents. Particularly preferred adjuvants are selected from the group comprising lactose, microcrystalline cellulose and/or magnesium stearate.

Furthermore, the micronutrient combination product can contain coating substances. The micronutrient combination product, in particular in form of a film-coated tablet, can contain coating substances suitable for film-coating selected from the group comprising cellulose and/or cellulose derivatives, hydroxypropyl cellulose, hydroxypropyl methylcellulose and/or microcrystalline cellulose, titanium dioxide, dyes, talcum, polymethacrylates, shellac, polyvinylpyrrolidone, polyvinyl alcohol, polyethylene glycols, triacetin, triethyl citrate, propylene glycol, glycerol, Arabic gum, silica, glycerol monostearate and/or cotton seed oil. Preferred are coating substances selected from the group comprising hydroxypropyl cellulose, hydroxypropyl methylcellulose, microcrystalline cellulose, glycerol, talcum, cotton seed oil, titanium dioxide and/or dyes.

Preferred dyes are selected from the group comprising iron oxides, indigo carmines, Al varnishes and/or carminic acid. Particularly preferred Al varnishes are selected from the group comprising Yellow Orange S Al varnish and/or Cochineal Red A Al varnish.

In preferred embodiments the micronutrient combination product in form of a film-coated tablet comprising a tablet core and a film coating comprises a film quantity in the range from 1 weight % to 12 weight %, preferably 2 weight % to 10 weight %, particularly preferably 5 weight % to 8 weight %, as related to the weight of the tablet core.

Furthermore, the micronutrient combination product can contain further additives that are common in the field of galenics and are compatible with the micronutrients.

Preferably, the micronutrients are employed in a form processible for the selected dosage form. Preferably, the micronutrient combination product contains vitamin E in form of vitamin E acetate. Preferably, the micronutrient combination product contains vitamin C in form of a granulate. Further preferably, the micronutrient combination product contains vitamin C in form of ascorbic acid. In particularly preferred embodiments, the micronutrient combination product contains zeaxanthin, lutein, zinc gluconate, copper (II) gluconate, vitamin E acetate, ascorbic acid, cellulose, lactose, and/or magnesium stearate.

In a preferred embodiment, the micronutrient combination product comprises the following agents, as related to one daily dose of the micronutrient combination product:
 a. 12 mg lutein;
 b. 0.6 mg zeaxanthin;
 c. 150 mg vitamin C;
 d. 15 mg vitamin E;
 e. 0.4 mg copper;
 f. 20 mg zinc.

The micronutrient combination product can also contain additives, accompanying substances, and/or raw materials, which are heavier than the actual agents, so that the given quantities as related to one daily dose or single dose can be lower or also higher.

In a preferred embodiment, the micronutrient combination product comprises the following agents, as related to one single dose of the micronutrient combination product:
 a. 6 mg lutein;
 b. 0.3 mg zeaxanthin
 c. 75 mg vitamin C;
 d. 7.5 mg vitamin E;
 e. 0.2 mg copper;
 f. 10 mg zinc.

In the sense of the present application, a single dose is understood to denote one administration unit of the micronutrient combination product; a single dose of the micronutrient combination product, for example, corresponds to one tablet, one film-coated tablet, one sugar-coated pill, one capsule, or one single administration unit of another form of preparation, like powder or granulate. In the sense of the present application, a daily dose is understood to denote the quantity of the micronutrient combination product that is administered per day.

Preferably, the daily dose and/or single dose is distributed to several identical or different forms of preparation, wherein the forms of preparation can contain identical or different agents and/or weight contents of agents.

The micronutrient combination product can be employed for producing a means for the dietetic prevention and/or treatment of diseases of the eye, preferably in cases of age-related macular degeneration. The micronutrient combination product according to the present invention is further suitable as a means for a supplementary balanced diet.

The term "dietetic treatment" (diätetische Behandlung) is explained in more detail in the EU Directive 1999/21/EG, which has been implemented in German Law on Jan. 1, 2002, as the $10^{th}$ Regulation on the Alteration of Diet Regulation ("10. Verordnung zur Änderung der Diätverordnung").

Owing to the advantageous agents of the micronutrient combination product, the latter can also be employed within the scope of a dietetic nutritional consultation as a means for a supplementary balanced diet, in particular food. Preferably, the micronutrient combination product can be employed for a supplementary balanced diet in cases of age-related macular degeneration. It has been shown that, in particular, impending nutrient deficiency in people at an advanced age can be equalized.

Examples for micronutrient combination products are provided in the following:

It is understood that the forms of preparation selected from the group comprising tablets, film-coated tablets, sugar-coated pills, capsules, powders, granulates, solutions, and/or effervescent tablets contain the customary adjuvants employed for formulating the respective forms of preparation, so that only the agents contained can be listed in the Examples.

EXAMPLE 1

Micronutrient combination product comprising 1 film-coated tablet containing the following agents:
 6 mg lutein;
 0.3 mg zeaxanthin
 75 mg vitamin C;
 7.5 mg vitamin E;
 0.2 mg copper;
 10 mg zinc.

EXAMPLE 2

Micronutrient combination product, daily dose comprising 2 film-coated tablets, each containing the following agents:
 6 mg lutein;
 0.3 mg zeaxanthin
 75 mg vitamin C;
 7.5 mg vitamin E;

0.2 mg copper;
10 mg zinc.

EXAMPLE 3

Film-coated tablet at 635 mg each, comprising the following agents:
6 mg lutein;
0.3 mg zeaxanthin
75 mg vitamin C;
7.5 mg vitamin E;
0.2 mg copper;
10 mg zinc,
wherein hypromellose, hydroxypropyl cellulose, glycerol, Yellow Orange Varnish S, Cochineal Red Varnish A, titanium dioxide, and talcum are contained as adjuvants and wherein the tablet core constitutes 600 mg and the coating film constitutes 35 mg.

The invention claimed is:

1. A micronutrient combination product consisting of: 0.1-2 mg of zeaxanthin, 2-40 mg of lutein, 1-80 mg of a form of zinc, 0.02-2 mg of a form of copper, 50-500 mg of a form of vitamin C, 2-60 mg of a form of vitamin E, an adjuvant, and optionally a coating substance; wherein the micronutrient combination product consists of a daily dosage administrable to a subject and suitable for equalizing a deficit of antioxidants caused by risk factors of smoking, alcohol drinking, stress or UV radiation.

2. The micronutrient combination product according to claim 1, wherein the adjuvant is selected from the group consisting of lactose, povidone, cellulose, cellulose derivatives, microcrystalline cellulose, starch, starch derivatives, magnesium stearate, stearic acid, gelatin, sodium aluminum silicate, silica, maltodextrin, dextrose, talcum, titanium dioxide, calcium carbonate, vegetable fats, tricalcium phosphate, antioxidants, stabilizers, Arabic gum, calcium phosphates, calcium silicate, sucrose, sodium citrate, citric acid, and gustatory corrigents.

3. The micronutrient combination product according to claim 1; wherein the coating substance is selected from the group comprising cellulose, cellulose derivatives, hydroxypropyl cellulose, hydroxypropyl methylcellulose, microcrystalline cellulose, titanium dioxide, dyes, talcum, polymethacrylates, shellac, polyvinylpyrrolidone, polyvinyl alcohol, polyethylene glycols, triacetin, triethyl citrate, propylene glycol, glycerol, Arabic gum, silica, glycerol monostearate, and cotton seed oil.

4. The micronutrient combination product according to claim 1, wherein said zinc consists of zinc gluconate, said copper consists of copper (II) gluconate, said vitamin E consists of vitamin E acetate, and said vitamin C consists of ascorbic acid.

5. A micronutrient combination product, consisting of: 0.1-2 mg of zeaxanthin, 2-40 mg of lutein, 1-80 mg of zinc, 0.02-2 mg of copper, 50-500 mg of vitamin C, 2-60 mg of vitamin E, an adjuvant, and optionally a coating substance; wherein the micronutrient combination product consists of a daily dosage administrable to a subject and suitable for equalizing a deficit of antioxidants caused by risk factors of smoking, alcohol drinking, stress or UV radiation; wherein the micronutrient combination product is in a form of a solid, a liquid, or a gel.

6. A micronutrient combination product, consisting of: 0.1-2 mg of zeaxanthin, 2-40 mg of lutein, 1-80 mg of zinc, 0.02-2 mg of copper, 50-500 mg of vitamin C, 2-60 mg of vitamin E, an adjuvant, and optionally a coating substance; wherein the micronutrient combination product consists of a daily dosage administrable to a subject and suitable for equalizing a deficit of antioxidants caused by risk factors of smoking, alcohol drinking, stress or UV radiation; wherein the micronutrient combination product is a solid having a core of from 200 mg to 1000 mg.

7. A micronutrient combination product consisting of:
12 mg lutein;
0.6 mg zeaxanthin;
150 mg vitamin C;
15 mg vitamin E;
0.4 mg copper;
20 mg zinc; and
an adjuvant;
wherein the micronutrient combination product is one daily dose.

8. A micronutrient combination product that consists of two units, each unit consisting of:
6 mg lutein;
0.3 mg zeaxanthin;
75 mg vitamin C;
7.5 mg vitamin E;
0.2 mg copper;
10 mg zinc; and
an adjuvant;
wherein the micronutrient combination product is one daily dose.

* * * * *